(12) United States Patent
Segard et al.

(10) Patent No.: US 10,376,895 B2
(45) Date of Patent: Aug. 13, 2019

(54) AGITATOR SHAFT FOR A GRINDING MILL

(71) Applicant: Corbion Biotech, Inc., South San Francisco, CA (US)

(72) Inventors: David Segard, Lestrem (FR); Samuel Patinier, Quesnoy sur Deule (FR)

(73) Assignee: CORBION BIOTECH, INC., South San Francisco, CA (US)

( * ) Notice: Subject to any disclaimer, the term of this patent is extended or adjusted under 35 U.S.C. 154(b) by 306 days.

(21) Appl. No.: 15/319,087

(22) PCT Filed: Jun. 23, 2015

(86) PCT No.: PCT/FR2015/051684
§ 371 (c)(1),
(2) Date: Dec. 15, 2016

(87) PCT Pub. No.: WO2015/197972
PCT Pub. Date: Dec. 30, 2015

(65) Prior Publication Data
US 2017/0136470 A1   May 18, 2017

(30) Foreign Application Priority Data
Jun. 25, 2014 (FR) .................................... 14 55925

(51) Int. Cl.
*B02C 17/00* (2006.01)
*B02C 17/16* (2006.01)
(Continued)

(52) U.S. Cl.
CPC .......... *B02C 17/163* (2013.01); *B02C 17/166* (2013.01); *B02C 17/168* (2013.01);
(Continued)

(58) Field of Classification Search
CPC ... B02C 17/163; B02C 17/165; B02C 17/166; B02C 17/168; C12M 47/02; C12M 47/06; B08B 3/102; B08B 9/0817
See application file for complete search history.

(56) References Cited

U.S. PATENT DOCUMENTS 3,844,490 A    10/1974  Mercier
4,813,617 A *   3/1989  Knox, Jr. .................. B02C 9/00
                                                    241/33

(Continued)

FOREIGN PATENT DOCUMENTS

GB         2 268 426 A     1/1994
WO       2014/005570 A2    1/2014

OTHER PUBLICATIONS

International Search Report, dated Oct. 30, 2015, from corresponding PCT application.

*Primary Examiner* — Faye Francis
(74) *Attorney, Agent, or Firm* — Leydig, Voit & Mayer

(57) ABSTRACT

An agitator shaft (1) for a grinding mill, including: —an axle (2) intended to be driven in rotation, —a succession of flat agitator elements (3) and tubular spacers (4) mounted in alternation on the axle and in a stack along the axle (2), —end stops (5, 6), secured to the axle, that keep the stack of agitator elements and spacers under compression, characterized in that the tubular spacers (4) have orifices allowing the free circulation of material and fluids from the outside of the agitator shaft to the inside, and vice versa.

14 Claims, 4 Drawing Sheets

(51) Int. Cl.
  *B08B 3/10* (2006.01)
  *B08B 9/08* (2006.01)
  *C12M 1/06* (2006.01)
  *C12M 1/00* (2006.01)

(52) U.S. Cl.
  CPC ............ *B08B 3/102* (2013.01); *B08B 9/0817* (2013.01); *C12M 27/02* (2013.01); *C12M 47/06* (2013.01); *B02C 2017/165* (2013.01)

(56) References Cited

U.S. PATENT DOCUMENTS

| | | | |
|---|---|---|---|
| 5,785,262 A | | 7/1998 | Tippett |
| 5,882,146 A | | 3/1999 | Inkyo et al. |
| 6,010,085 A | * | 1/2000 | Angeletakis ............ B02C 17/16 241/182 |
| 6,607,152 B2 | * | 8/2003 | Yanase ................... B02C 17/06 241/172 |
| 7,559,493 B1 | * | 7/2009 | Hockmeyer .......... B02C 17/181 241/171 |
| 8,376,252 B1 | * | 2/2013 | Hockmeyer .......... B02C 17/168 241/172 |
| 9,283,565 B2 | * | 3/2016 | Greenwood .......... B02C 17/181 |
| 2005/0011976 A1 | | 1/2005 | Sneeringer et al. |
| 2014/0224357 A1 | * | 8/2014 | Greenwood .......... B02C 17/168 137/544 |
| 2015/0102139 A1 | | 4/2015 | Nied et al. |

\* cited by examiner

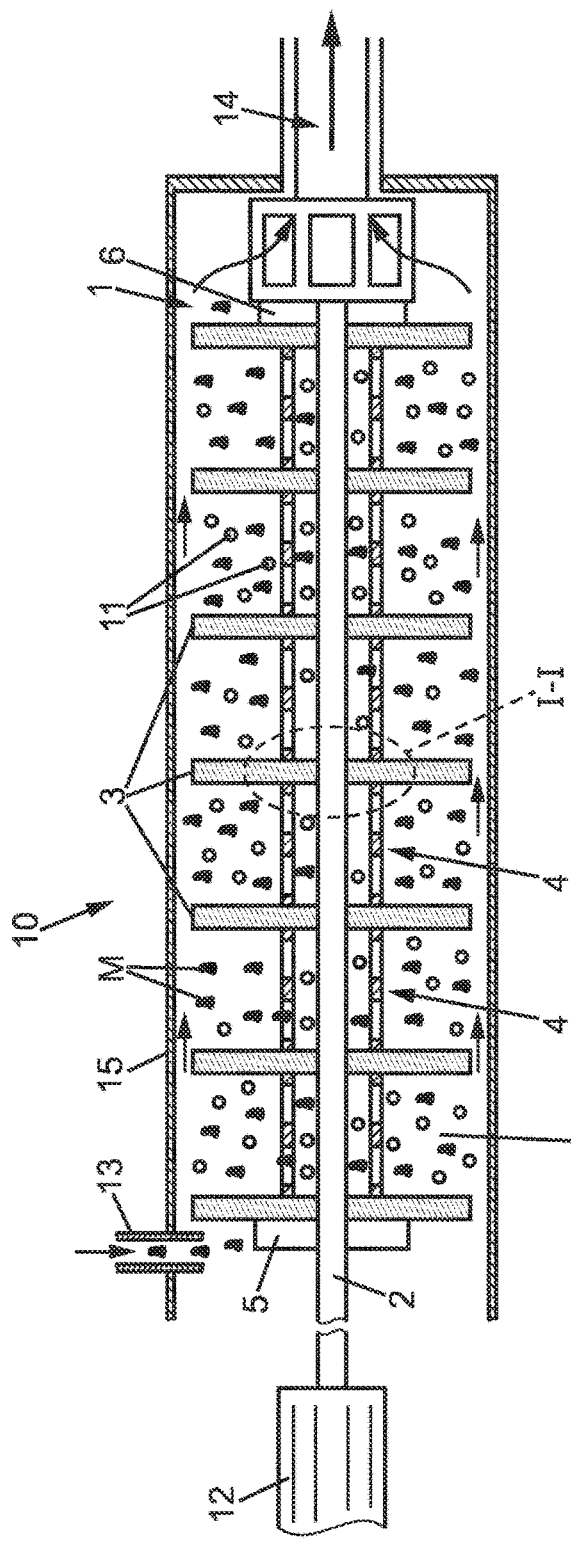
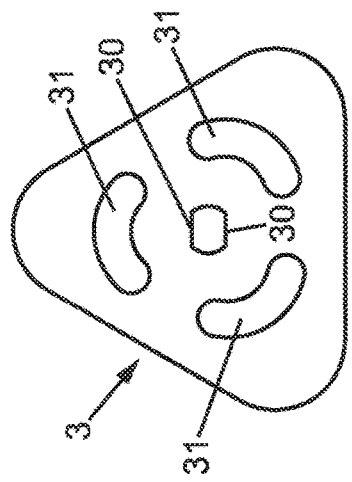
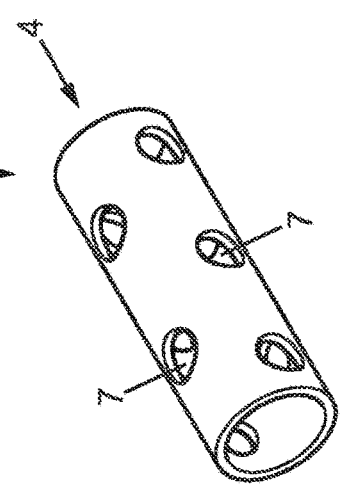
FIG. 1
FIG. 1a
FIG. 1b

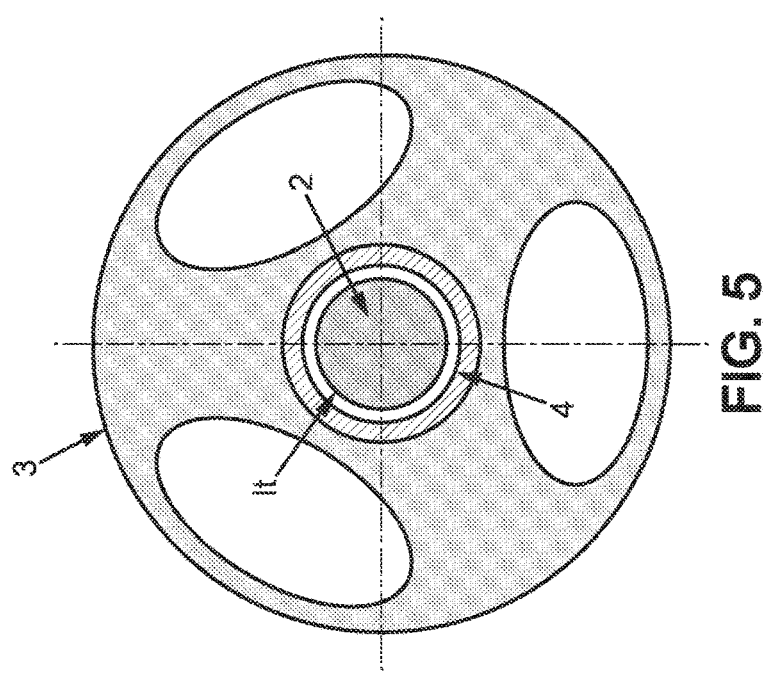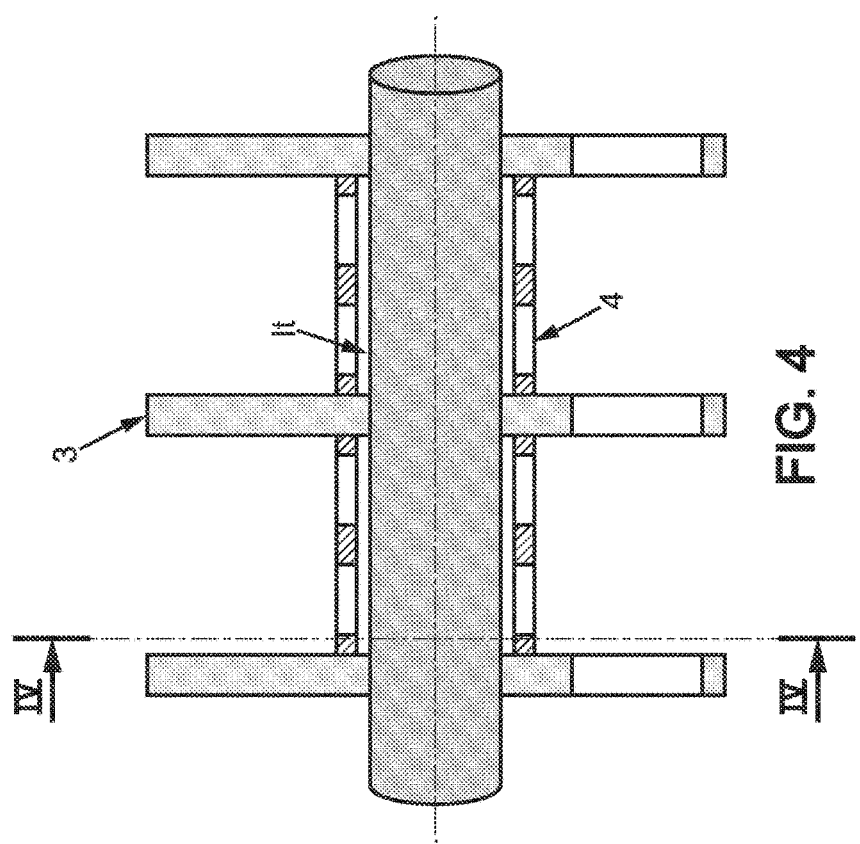

AGITATOR SHAFT FOR A GRINDING MILL

The invention relates to an agitator shaft and to a mill equipped with such an agitator shaft. Such an agitator shaft and mill will find a particular application for the lysis of biomasses of microorganisms produced on an industrial scale, notably by fermentation, such as microalgae, more particularly microalgae of the genus *Chlorella*.

The field of the invention is that of bead mills which conventionally comprise a treatment chamber defined by the internal volume of a, typically cylindrical, tank, inside which it is possible to grind matter such as cellular microorganisms by the dry method, or in a liquid medium. The lysis of single-cell microorganisms is obtained through the effect of shear forces that result from the grinding and from the mutual collision of small beads inside the chamber, which are set in motion by an agitator shaft of the mill, which is driven in rotation on its spindle under the action of a geared motor.

The documents U.S. Pat. Nos. 3,844,490, 5,785,262, US2005/0011976 and WO 2014/005570 disclose such, horizontal-spindle or vertical-spindle, bead mills. The agitator shaft of a bead mill conventionally comprises, as illustrated in the cross-sectional view in FIG. 1 of the document WO2014/005570, a central spindle, along which agitator elements which are generally flat and substantially perpendicular to the spindle are distributed, these being referred to below as "agitator disks" for the sake of simplification. It is known practice to space these agitator disks apart from one another by virtue of tubular spacers that are mounted around the spindle and each bear at their ends against two successive agitator disks of the shaft.

The assembly of such an agitator shaft consists essentially in successively threading the spacers and agitator disks alternately onto the central spindle until they come into contact. The stack of spacers and agitator disks is held between two end stops which are secured to the central spindle and the spacing of which is maintained by a clamp system. Usually, rods (or steel strips) pass through grooves in the agitator disks, at the inside diameter, with the aim of causing the spindle and the agitator disks to rotate as one.

For example, and in the document US 2005/0011976 A1, FIG. 12, the agitator disks are referenced 22, the central spindle is referenced 24 and the spacers are referenced 20. As can be seen in the cross-sectional view in FIG. 1 of the document WO 2014/005570, the agitator shaft comprises a free interstitial volume, defined between the outer surface of the central spindle and the inner walls of the tubular spacers, agitator disks, and an end plate (at the right in FIG. 1). As can be seen in this same figure, the beads are disposed in the treatment chamber, with the matter to be ground, in the treatment volume defined between the inner wall of the tank and the outer surface of the agitator shaft.

By contrast, the agitator shaft is sealed so as to prevent any matter and beads from passing into the cavity of the agitator shaft. In particular, the assembly of the various elements (spacers, agitator disks, central spindle, end plate) is a sealed assembly: the spacers are tubular, with solid walls, the sealing with respect to fluids being supplemented by seals between the spacer/agitator disk bearing surfaces, said seals being compressed during clamping. Sealing washers (made of copper) are combined with the screws used for clamping the end plate so as to prevent any leakage along said screws, through the end plate.

The present Applicant has carried out performance tests on such a bead mill. In particular, the desired aim was that of lysing single-cell microorganisms (microalgae of the *chlorella* type), cultured in a bioreactor at a concentration of 300 grams to 400 grams (of dry matter) per liter. Microalgae, in liquid medium, are fed in, at a constant rate, at the feed opening of the bead mill, at one of the ends of the chamber. In the treatment chamber, these microalgae are lysed through the action of the beads which are moved around by the agitator shaft, which is driven on its spindle at a speed of around 1000 rpm, the ground cells continuously exiting at the other end of the chamber.

Microalgae of the *chlorella* type are organisms that are extremely sensitive to contamination notably of bacterial origin; it is imperative that satisfactory operating conditions be maintained so as to avoid any contamination during grinding operations. The occurrence of contamination is unacceptable and involves discarding the contents, and then sterilizing the installation before implementing a new production operation. Contamination thus results in considerable downtime.

In this regard, and according to the inventor's findings, the design of the agitator shaft as known from the prior art is at risk in that a lack of sealing of the shaft would allow matter to pass into the cavity of the shaft and stagnate therein, thereby promoting the occurrence of contamination inside the shaft, which, on account of this same defect, would spread, in return, to the matter in the treatment chamber.

During tests, the present Applicant thus carefully examined the sealing of the agitator shaft. In particular, and under the abovementioned conditions, it became apparent that the agitator shaft was not perfectly sealed.

The aim of the present invention is to propose an agitator shaft for a bead mill which remedies the abovementioned drawbacks, in particular which eliminates the risk of contamination as can be encountered in prior art agitator shafts.

Another aim of the present invention is to propose such an agitator shaft which requires simpler maintenance in use.

Further aims and advantages of the present invention will become apparent from the following description which is given only by way of entirely nonlimiting example.

First of all, the invention relates to an agitator shaft for a mill, comprising:
  a spindle intended to be driven in rotation,
  a series of flat agitator elements and tubular spacers that are mounted in alternation on the spindle and in a stack along said spindle,
  end stops that are secured to the spindle and keep the stack of agitator elements and spacers under compression.

According to the invention, the tubular spacers have orifices that allow the fluids and matter to flow freely from the outside of the agitator shaft to the inside, and vice versa.

According to optional features of the invention, considered alone or in combination:
  the tubular spacers are one-piece elements;
  the orifices have diameters of between 4 mm and 50 mm, preferably between 20 mm and 30 mm;
  the orifices are smooth, or chamfered beforehand;
  the agitator elements are rotationally linked to the spindle by virtue of flats between the spindle and the agitator elements, or alternatively by steel strips;
  the spindle is made of stainless steel grade 1.4418 or X4CrNiMo16.5.1 according to the Euronorm standard;
  the agitator elements each comprise a plate provided with a central orifice for the passage of the spindle, substantially perpendicular to the spindle, and preferably through-recesses distributed around said spindle;
  the spacers bear against the faces of the agitator elements with their ends, by way of seals between the bearing faces of the spacers, for the one part, and the bearing faces of the agitator elements, for the other part.

The invention also relates to a bead mill comprising a tank that holds an agitator shaft in accordance with the invention. Preferably, the orifices in the spacers have a larger size than that of the beads so as to allow the beads to flow freely from the outside of the agitator shaft to the inside, and vice versa.

The invention will be understood better from reading the following description which is accompanied by the appended drawings, in which:

FIG. 1 is a schematic view, on a section plane passing through the spindle, of a bead mill in accordance with the invention, which is equipped with an agitator shaft according to the invention.

FIG. 1a is a detail view, in perspective, of a perforated spacer according to the invention, with which the agitator shaft of the mill in FIG. 1 is equipped.

FIG. 1b is a detail view, from the front, of an agitator element with which the agitator shaft of the mill in FIG. 1 is equipped.

FIG. 4 is a see-through view of a section of length of the agitator shaft.

FIG. 5 is a view on the section line Iv-Iv as illustrated in FIG. 4.

Figure 2:
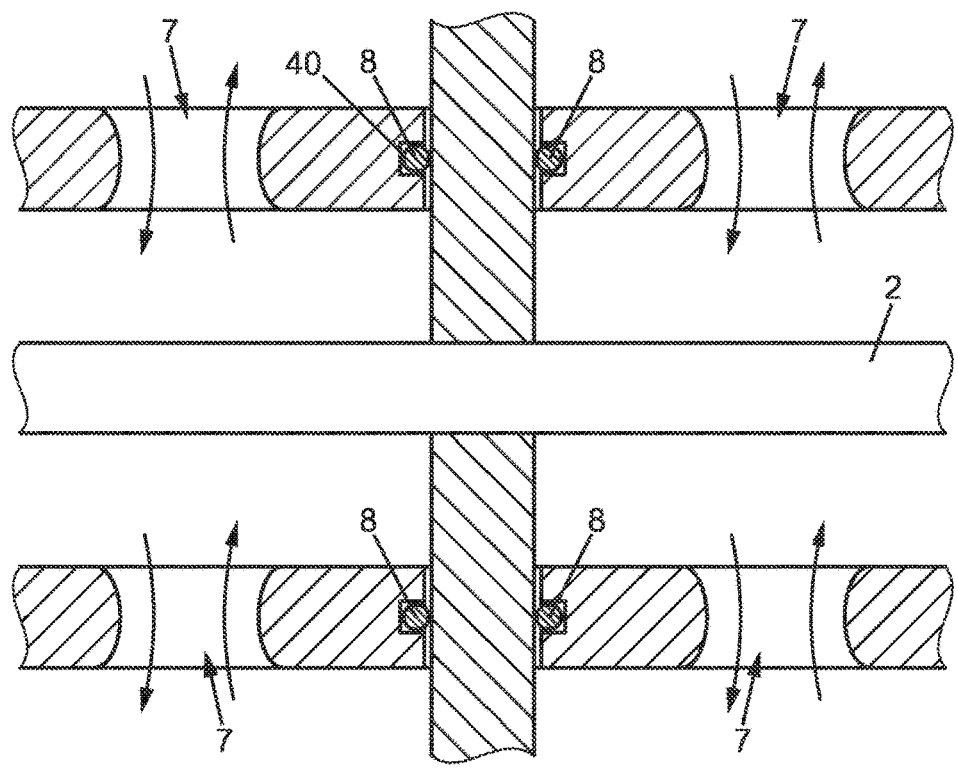
FIG. 2 is a detail view of the frame I-I as illustrated in FIG. 1.

First of all, the invention relates to an agitator shaft 1 for a mill, comprising:
- a spindle 2 intended to be driven in rotation, typically by a geared motor 12,
- a series of flat agitator elements 3 and tubular spacers 4 that are mounted in alternation on the spindle and in a stack along said spindle 2,
- end stops 5, 6 that are secured to the spindle and keep the stack of agitator elements 3 and spacers 7 under compression.

Such an assembly is illustrated by way of nonlimiting example in FIG. 1. The assembly of such an agitator shaft consists essentially in successively threading the spacers 4 and agitator elements 3 alternately onto the central spindle 2 until they come into contact. The stack of spacers 4 and agitator elements 3 is held between the two end stops, referenced 5 on the left and 6 on the right, which are secured to the central spindle and the spacing of which is maintained by a clamp system.

The agitator elements 3 can each comprise a plate provided with a central orifice for the passage of the spindle 2, or preferably through-recesses 31 distributed around the spindle. Each of the agitator elements can have a noncircular contour, as illustrated in FIG. 1b, the agitator elements 3 preferably then being angularly offset, in alternation, along the length of the spindle 2.

Such an agitator shaft design is known from the prior art, in particular from the document WO 2014/005570. In such prior art that is known to the present Applicant, the agitator shaft is a shaft that is sealed so as to prevent matter from passing from the treatment chamber into the cavity of the agitator shaft.

However, tests carried out by the present Applicant, under the conditions mentioned in the introduction, have demonstrated that this sealing is not perfect, this lack of sealing constituting a risk of the occurrence of contamination.

As the inventor currently understands it, such a lack of sealing would be explained, during the tests carried out, by the high dynamic load which would be exerted on the agitator shaft, causing stresses (bending and/or twisting) that result in a loss of sealing.

The inventor considers that it would, of course, be possible to reinforce the sealing of the shaft by an improved design of the agitator shaft, for example by increasing the number of seals and the quality thereof. However, from the inventor's experience, the sealing of such an agitator shaft would always have to be periodically monitored, and would necessarily involve periodic, difficult and costly, maintenance operations such as changing seals.

The invention is the result of the inventor's finding that it is difficult to implement a sealed agitator shaft.

The solution proposed by the inventor is the complete opposite of what a person skilled in the art would do: since it appears difficult to provide perfect sealing of the agitator shaft, the solution proposed by the inventor is, by contrast, to provide largely permeable spacers so as to ensure the evacuation, emptying and cleaning of the free internal volume of the spacer.

The objective pursued here is thus to eliminate, in the agitator shaft, cavities inside the spacers, into which the matter and fluids can pass and then stagnate, contaminating in return the grinding chamber in return.

According to the invention, the tubular spacers 3 advantageously have orifices 7 that allow the fluids and matter to flow freely from the outside of the agitator shaft 1 to the inside, and vice versa. The orifices 7 have diameters of between 4 mm and 50 mm, preferably between 20 mm and 30 mm.

Preferably, these orifices 7 have sizes greater than the size of the beads 11 used in the mill 10. The free passage of the beads through the spacer 4 makes it possible, during operation, to ensure better cleanability of the internal cavities (interstice It) during operation.

Preferably, the geometry of the orifices 7 is designed so as to encourage the fluids and matter to be ground to flow from the outside of the spacer to the inside, and vice versa, while the agitator shaft is rotating.

The tubular spacers 4 can be one-piece elements which are, for example, cylindrical. The orifices can be produced by machining the wall of the tubular spacer. Preferably, these orifices 7 are smooth, or chamfered, so as to limit deposits as much as possible, and thus the occurrence and development of contamination.

However, according to the inventor's findings, this novel agitator shaft design, which is permeable to the fluids and matter to be ground and, preferably, to the grinding beads, has the defect of exposing the central spindle 2 to greater stresses than those that are encountered by a central spindle of a sealed agitator shaft as is known from the prior art. This is because the spindle of an agitator shaft according to the prior art is protected from the matter to be ground and from the grinding beads and is thus subjected to a lesser risk of corrosion.

In order to remedy this difficulty, the choice of material of the spindle 2 is important in that it determines not only its dynamic mechanical strength, in particular with regard to twisting and bending, but also its corrosion resistance. In order to increase the lifetime of the equipment, it is advantageously possible, according to the invention, to choose a stainless steel of which the mechanical performance and the performance with regard to corrosion meet these new, more demanding, constraints. To this end, the spindle 2 may be made of stainless steel grade 1.4418 or X4CrNiMo16.5.1 (or a martensitic steel) according to the Euronorm standard.

Figure 3:
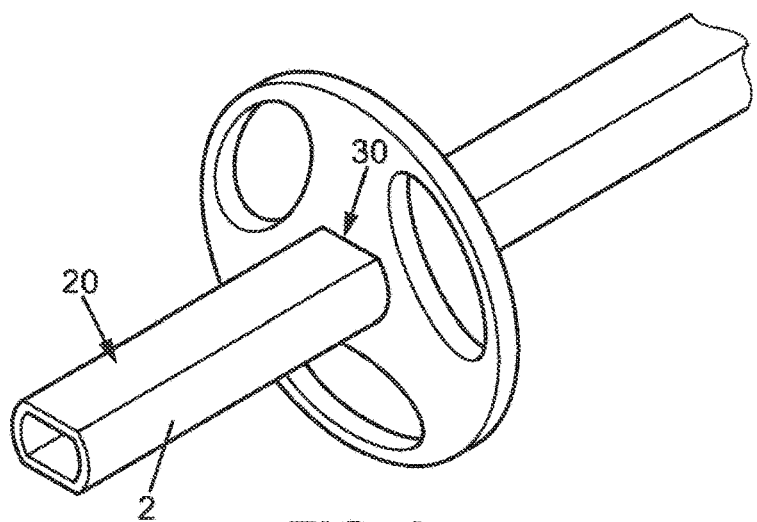
FIG. 3 is a schematic view illustrating the conjoint rotation between the spindle and one of the agitator elements by way of flats.
Figure 6:
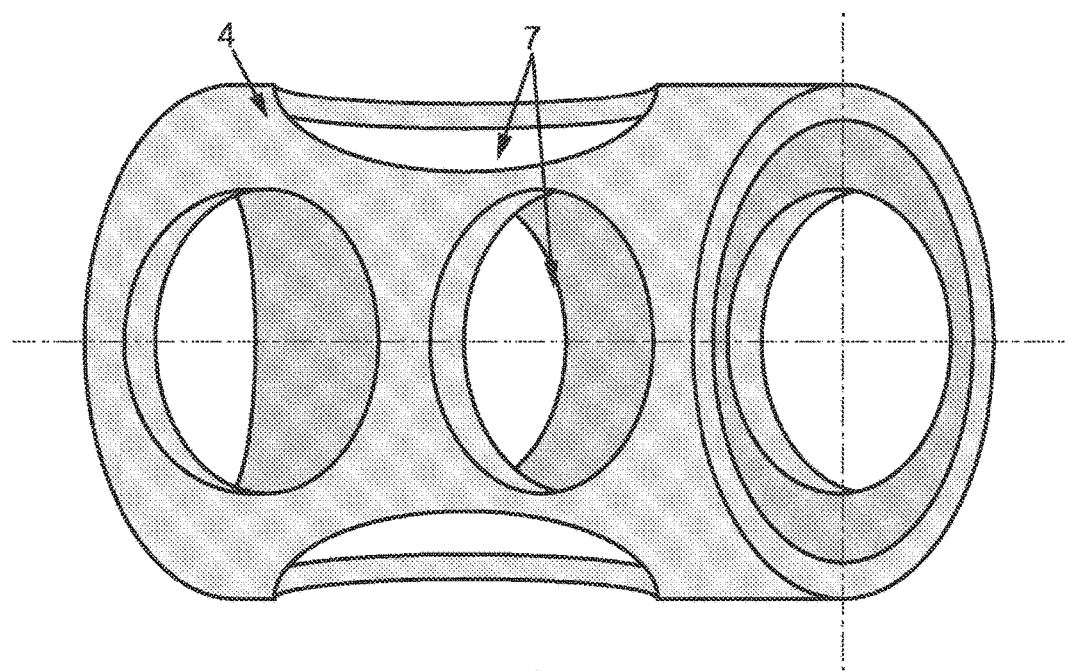
FIG. 6 is a detail view of the spacer from FIG. 4.

According to one embodiment, which is illustrated in a nonlimiting manner in FIG. 3, the agitator elements 3 may be rotationally linked to the spindle by virtue of flats 20, 30 between the spindle 2 and the agitator elements 3. In this case, the central orifice of the agitator elements allows the insertion of the spindle 2 to within the operating clearance. These flats 20 and 30 between the spindle 2 and the agitator element 3 cooperate so as to prevent any relative rotational motion between these two elements. Alternatively, steel strips can be used.

According to an embodiment that is not illustrated, the spacers 7 can bear directly (i.e. without seals) against the faces of the agitator elements 3 with their ends. According to an alternative embodiment, which is illustrated in a nonlimiting manner in FIG. 2, the spacers 7 bear against the faces of the agitator elements 3 with their ends, by way of seals 8 between the bearing faces of the spacers 4, for the one part, and the bearing faces of the agitator elements 3, for the other part. In such a case, the objective of these seals 8 is obviously not to ensure sealing with respect to the fluid, since the spacers are permeable to liquids. These seals 8 notably facilitate assembly by being more tolerant to the manufacturing dimensions of the various, namely the agitator elements and the spacers. These seals 8 can make it possible to limit the risk of the faces of the agitator elements being marked, at the bearing surface of the spacers 4. In order to avoid any squashing of the seals 8 during clamping, said seals 8 can be held partially in grooves 40 recessed into the bearing surfaces of the spacers 7. The seals 8 are circular, preferably annular, seals.

The invention also relates to a bead mill 10 comprising a tank 15 that holds an agitator shaft 1 in accordance with the invention. Preferably, the orifices 7 in the spacers 4 have a larger size than that of the beads 11 so as to allow the beads to flow freely from the outside of the agitator shaft 1 to the inside, and vice versa, during operation. The mill is preferably a horizontal-spindle mill.

It is preferably a mill for continuously treating matter, referenced M. The mill has an inlet 13 for the matter to be ground and an outlet 14 for the ground matter. Such a mill is preferably fed continuously at a given rate.

The invention finds a particular application as an industrial mill. The feed rate to the mill may be between 0.5 m³/h and 10 m³/h and for concentrations of matter (dry matter) of 300 g/l to 400 g/l, the agitator shaft 1 being subjected to high mechanical stresses under such conditions.

The maintenance of the mill may provide, notably between two production phases, for the internal walls of the tank 15, the internal and external walls of the agitator shaft 1, and the spindle 2 to be cleaned by supplying the mill with a cleaning solution. During this step, the agitator shaft 1 is preferably set in rotation so as to promote the flow of the cleaning solution through the agitator shaft 1 by way of the orifices 7.

Of course, further embodiments could have been envisaged by a person skilled in the art without thereby departing from the scope of the invention as defined hereinbelow.

PARTS LIST

1. Agitator shaft,
2. Spindle,
3. Agitator element,
4. Tubular spacers,
5,6. End stops,
7. Orifices (spacers),
8. Seal,
10. Bead mill,
11. Beads,
12. Geared motor,
13. Matter inlet (mill),
14. Matter outlet (mill),
15. Tank,
20. Flats (spindle),
30. Flats (agitator elements),
31. Recesses (agitator elements),
40. Grooves (for seal),
M. Matter,
It. Interstice (between spindle and spacer).

The invention claimed is:

1. An agitator shaft (1) for a mill, comprising:
    a spindle (2) intended to be driven in rotation,
    a series of flat agitator elements (3) and tubular spacers (4) that are mounted in alternation on the spindle and in a stack along the spindle (2),
    end stops (5, 6) that are secured to the spindle and keep the stack of agitator elements and spacers under compression,
    wherein the tubular spacers (4) have orifices (7) that allow matter and fluids to flow freely from outside of the agitator shaft to inside of the agitator shaft, and vice versa.

2. The agitator shaft as claimed in claim 1, wherein the tubular spacers (4) are one-piece elements.

3. The agitator shaft as claimed in claim 2, wherein the orifices (7) have diameters of between 20 mm and 30 mm.

4. The agitator shaft as claimed in claim 2, wherein the orifices (7) have diameters of between 4 mm and 50 mm.

5. The agitator shaft as claimed in claim 1, wherein the orifices (7) have diameters of between 4 mm and 50 mm.

6. The agitator shaft as claimed in claim 1, wherein the orifices (7) are smooth or chamfered.

7. The agitator shaft as claimed in claim 1, wherein the agitator elements (3) are rotationally linked to the spindle by virtue of flats (20, 30) between the spindle (2) and the agitator elements (3).

8. The agitator shaft as claimed in claim 1, wherein the spindle (2) is made of stainless steel grade 1.4418 or X4CrNiMo16.5.1 according to the Euronorm standard.

9. The agitator shaft as claimed in claim 1, wherein the agitator elements (3) each comprise a plate provided with a central orifice for passage of the spindle, substantially perpendicular to the spindle.

10. The agitator shaft as claimed in claim 1, wherein the agitator elements (3) comprise faces and the spacers (4) comprise ends, and wherein the spacers (4) bear against the faces of the agitator elements (3) with their ends, by way of seals (8) between (i) the ends of the spacers (4) and (ii) the bearing faces of the agitator elements (3).

11. A bead mill (10) comprising a tank that holds the agitator shaft (1) as claimed in claim 1.

12. The mill as claimed in claim 11, wherein the mill comprises beads (11) and the orifices (7) in the spacers (4) have a larger size than that of the beads (11) so as to allow the beads to flow freely from outside of the agitator shaft (1) to inside of the agitator shaft, and vice versa.

13. A method for cleaning the mill as claimed in claim 11, wherein the tank comprises internal walls and the agitator shaft comprises internal and external walls, the method comprising cleaning the internal walls of the tank (15) and the internal and external walls of the agitator shaft (1) by supplying the mill with a cleaning solution.

14. The method as claimed in claim 13, comprising setting the agitator shaft (1) in rotation such that the cleaning solution flows through the agitator shaft (1).

\* \* \* \* \*